United States Patent [19]
Barnes et al.

[11] Patent Number: 6,159,956
[45] Date of Patent: Dec. 12, 2000

[54] PROCESS AND INTERMEDIATE COMPOUNDS FOR THE PREPARATION OF DIFLUOROVINYLSILANE INSECTICIDAL AND ACARICIDAL AGENTS

[75] Inventors: Keith D. Barnes, Newtown, Pa.; Yulin Hu, Plainsboro, N.J.

[73] Assignee: American Cyanamid Co., Madison, N.J.

[21] Appl. No.: 09/112,115

[22] Filed: Jul. 8, 1998

[51] Int. Cl.[7] .............................. A01N 55/10; C07F 7/14; C07F 7/16
[52] U.S. Cl. ............................ 514/63; 556/466; 556/478; 556/485
[58] Field of Search ..................... 556/478, 485; 514/63

[56] References Cited

U.S. PATENT DOCUMENTS

| | | | |
|---|---|---|---|
| 4,481,366 | 11/1984 | Hiyama et al. | 556/431 |
| 5,710,102 | 1/1998 | Barnes et al. | 504/193 |

OTHER PUBLICATIONS

J. Org. Chem., 53, pp. 2714–2720 (1988).
J. Am. Chem. Soc., 108, pp. 4229–4230 (1986).
Tetrahedron, 50(10), pp. 2293–3063 (1994).

*Primary Examiner*—Joseph McKane
*Assistant Examiner*—Jane C. Osowecki
*Attorney, Agent, or Firm*—Barbara L. Renda; Barbara V. Maurer

[57] ABSTRACT

The present invention provides an improved process and intermediate compounds for the preparation of difluorovinylsilane insecticide and acaricidal agents of the formula I

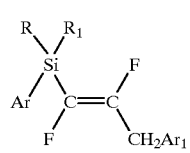

(I)

wherein
Ar is phenyl, 1- or 2-napthyl or a 5- or 6-membered heteroaromatic ring, each of which may be optionally substituted by any combination of from one to three halogen, $C_1$–$C_4$alkyl, $C_1$–$C_4$haloalkyl, $C_1$–$C_4$alkoxy, haloalkoxy, $C(O)R_2$ or $S(O)_nR_3$ groups,
R and $R_1$ are each independently $C_1$–$C_4$alkyl or $C_3$–$C_5$cycloalkyl;
$Ar_1$ is phenoxyphenyl, phenyl, biphenyl, phenoxypyridyl, benzylpyridyl, benzylphenyl,
  1- or 2-napthyl or a 5- or 6-membered heteroaromatic ring, each of which may be optionally substituted by any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
n is an integer of 0, 1 or 2;
$R_2$ and $R_4$ are each independently $C_1$–$C_4$alkyl, benzyl or phenyl;
$R_3$ is $C_1$–$C_4$alkyl or $C_1$–$C_4$haloalkyl; and
the fluorine atoms attached to the double bond are trans with respect to each other.

11 Claims, No Drawings

PROCESS AND INTERMEDIATE COMPOUNDS FOR THE PREPARATION OF DIFLUOROVINYLSILANE INSECTICIDAL AND ACARICIDAL AGENTS

BACKGROUND OF THE INVENTION

Difluorovinylsilane compounds which are useful as insecticide and acaricidal agents, and a process for their preparation, are described in U.S. Pat. No. 5,710,102. However, the process described in U.S. Pat. No. 5,710,102 is not entirely satisfactory because the difluorovinylsilane compounds are produced in relatively low yields. Accordingly, a need exists in the art for an improved process for the preparation of these compounds.

It is, therefore, an object of the present invention to provide an improved process for the preparation of difluorovinylsilane compounds.

It is also an object of the present invention to provide intermediate compounds useful in the preparation of difluorovinylsilane compounds.

Other objects and advantages of the present invention will be apparent to those skilled in the art from the description below and the appended claims.

SUMMARY OF THE INVENTION

The present invention provides an improved process for the preparation of a difluorovinylsilane compound of the formula I

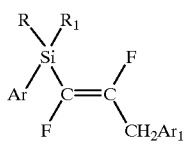

(I)

wherein
Ar is phenyl, optionally substituted with any combination of from one to three halogen, $C_1$–$C_4$alkyl, $C_1$–$C_4$haloalkyl, $C_1$–$C_4$alkoxy, $C_1$–$C_4$haloalkoxy, $C(O)R_2$ or $S(O)_nR_3$ groups,
  1- or 2-naphthyl, optionally substituted with any combination of from one to three halogen, $C_1$–$C_4$alkyl, $C_1$–$C_4$-haloalkyl, $C_1$–$C_4$alkoxy, $C_1$–$C_4$haloalkoxy, $C(O)R_2$ or $S(O)_nR_3$ groups, or
  a 5- or 6-membered heteroaromatic ring, optionally substituted with any combination of from one to three halogen, $C_1$–$C_4$alkyl, $C_1$–$C_4$haloalkyl, $C_1$–$C_4$alkoxy, $C_1$–$C_4$haloalkoxy, $C(O)R_2$ or $S(O)_nR_3$ groups;
R and $R_1$ are each independently $C_1$–$C_4$alkyl or $C_3$–$C_5$-cycloalkyl;
$Ar_1$ is phenoxyphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  phenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  biphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  phenoxypyridyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  benzylpyridyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  benzylphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups,
  1- or 2-naphthyl, optionally substituted with any combination of from one to three halogen, $C_1$–$C_4$alkyl, $C_1$–$C_4$haloalkyl, $C_1$–$C_4$alkoxy, $C_1$–$C_4$haloalkoxy or $C(O)R_4$ groups, or
  a 5- or 6-membered heteroaromatic ring, optionally substituted with any combination of from one to three halogen, $C_1$–$C_4$alkyl, $C_1$–$C_4$haloalkyl, $C_1$–$C_4$alkoxy, $C_1$–$C_4$haloalkoxy or $C(O)R_4$ groups;
n is an integer of 0, 1 or 2;
$R_2$ and $R_4$ are each independently $C_1$–$C_4$alkyl, benzyl or phenyl; and
$R_3$ is $C_1$–$C_4$alkyl or $C_1$–$C_4$haloalkyl; and the fluorine atoms attached to the double bond are trans with respect to each other,
which process comprises:
  (a) reacting a 3-aryl-1,1,2-trifluoro-1-propene compound of the formula II

(II)

wherein $Ar_1$ is as described above with a reducing agent to form a 3-aryl-1,2-difluoro-1-propene compound a the formula III

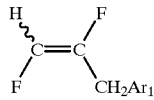

(III)

wherein the fluorine atoms attached to the double bond are predominately trans with respect to each other;
  (b) reacting the 3-aryl-1,2-difluoro-1-propene compound with a lithium base to form a 3-aryl-1,2-di-fluoro-1-propenyllithium compound of the formula IV

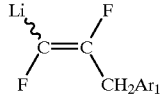

(IV)

wherein the fluorine atoms attached to the double bond are predominately trans with respect to each other; and
  (c) reacting the 3-aryl-1,2-difluoro-1-propenyl-lithium compound with an arylchlorosilane compound of the formula V

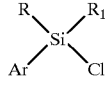

(V)

wherein Ar, R and $R_1$ are as described above.

The present invention also relates to the intermediate 3-aryl-1,1,2-trifluoro-1-propene; 3-aryl-1,2-difluoro-1-propene; and 3-aryl-1,2-difluoro-1-propenyllithium compounds.

DETAILED DESCRIPTION OF THE INVENTION

A preferred embodiment of the present invention comprises reacting a 3-aryl-1,1,2-trifluoro-1-propene compound of formula II with a reducing agent, preferably at a temperature ranging from about −50° C. to 50° C., more preferably from about −10° C. to 25° C., in the presence of a first solvent, to form a 3-aryl-1,2-difluoro-1-propene compound of formula III, reacting the formula III compound with a lithium base, preferably at a temperature ranging from about −100° C. to 0° C., more preferably from about −70° C. to −50° C., in the presence of a second solvent to form a 3-aryl-1,2-difluoro-1-propenyllithium compound of formula IV, and reacting the formula IV compound in situ with an arylchlorosilane compound of formula V, preferably at a temperature ranging about −100° C. to 50° C., more preferably about −70° C. to 30° C.

The present invention also relates to the 3-aryl-1,1,2-trifluoro-1-propene, 3-aryl-1,2-difluoro-1-propene, and 3-aryl-1,2-difluoro-1-propenyllithium compounds which are utilized in the process of this invention. Those compounds may be represented by the structural formula VI

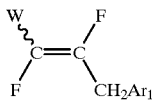

(VI)

wherein
W is H, F or Li;
Ar$_1$ is phenoxyphenyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    phenyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    biphenyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    phenoxypyridyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    benzylpyridyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    benzylphenyl, optionally substituted with any combination of from one to five halogen, C$_1$–C$_4$alkyl, C$_1$–C$_4$haloalkyl, C$_1$–C$_4$alkoxy, C$_1$–C$_4$haloalkoxy or C(O)R$_4$ groups,
    1- or 2-naphthyl, optionally substituted with any combination of from one to three halogen, C$_1$–C$_4$alkyl, C$_1$–C$_4$haloalkyl, C$_1$–C$_4$alkoxy, C$_1$–C$_4$haloalkoxy or C(O)R$_4$ groups, or
    a 5- or 6-membered heteroaromatic ring, optionally substituted with any combination of from one to three halogen, C$_1$–C$_4$alkyl, C$_1$–C$_4$haloalkyl, C$_1$–C$_4$alkoxy, C$_1$–C$_4$haloalkoxy or C(O)R$_4$ groups; and
R$_4$ is C$_1$–C$_4$alkyl, benzyl or phenyl; and when W is H or Li, the fluorine atoms attached to the double bond are predominately trans with respect to each other.

Preferred formula VI compounds are those wherein W is H, F or Li; and
Ar$_1$ is 3-phenoxyphenyl, optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups,
    phenyl, optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups, or
    biphenyl, optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups.

Especially preferred intermediate compounds of formula VI are those wherein W is H, F or Li; and
Ar$_1$ is 3-phenoxyphenyl, optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups.

Most preferred compounds of formula VI are those which are especially useful for the preparation of highly active difluorovinylsilane insecticide and acaricidal agents, and are those wherein
W is H, F or Li; and
Ar$_1$ is 3-phenoxyphenyl, 4-fluoro-3-phenoxyphenyl or 3-(4-fluorophenoxy)phenyl.

In formula I above, 5- and 6-membered heteroaromatic rings include contain 1-3 nitrogen, oxygen or sulfur atoms, and, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings, each optionally substituted as described in formula I above.

Exemplary of halogen hereinabove are fluorine, chlorine, bromine and iodine. The term "C$_1$–C$_4$alkyl" and "C$_1$–C$_4$alkoxyl" refer to straight or branched chain alkyl or alkoxy groups containing from one to four carbon atoms and are exemplified by methyl, methoxy, ethyl, ethoxy, propyl, propoxy, butyl, butoxy, and their branched chain counterparts. The terms "C$_1$–C$_4$haloalkyl" and "C$_1$–C$_4$haloalkoxy" are defined as a straight or branched chain C$_1$–C$_4$alkyl group, and a C$_1$–C$_4$alkoxy group substituted with one or more halogen atoms, respectively. Representative compounds preparable by the process of the present invention include:

1-[(p-chlorophenyl)dimethylsilyl]-1,2-difluoro-3-(m-phenoxyphenyl)-1-propene, (Z)-;
1-[(p-chlorophenyl)dimethylsilyl]-1,2-difluoro-3-(4-fluoro-3-phenoxyphenyl)-1-propene, (Z)-;
1-[(p-ethoxyphenyl)dimethylsilyl]-1,2-difluoro-3-(m-phenoxyphenyl)-1-propene, (Z)-;
1-[(p-ethoxyphenyl)dimethylsilyl]-1,2-difluoro-3-(4-fluoro-3-phenoxyphenyl)-1-propene, (Z)-;
1-[(p-ethoxyphenyl)dimethylsilyl]-1,2-difluoro-3-(2-methyl-3-biphenylyl)-1-propene, (Z)-;
1,2-difluoro-1-[(p-fluorophenyl)dimethylsilyl]-3-(m-phenoxyphenyl)-1-propene, (Z)-;
3-[3-(p-chlorophenoxy)phenyl]-1-[(p-ethoxyphenyl) dimethylsilyl]-1,2-difluoro-1-propene, (Z)-;
1,2-difluoro-3-(4-fluoro-3-phenoxyphenyl)-1-[(p-fluorophenyl)dimethylsilyl]-1-propene, (Z)-.
1,2-difluoros-1-(phenyldimethylsilyl)-3-(4-fluoro-3-phenoxyphenyl)-1-propene, (Z)-;
1-[(p-trifluoromethylphenyl)dimethylsilyl]-1,2-difluoro-3-(4-fluoro-3-phenoxyphenyl)-1-propene, (Z)-;
1-[(p-trifluoromethylphenyl)dimethylsilyl]-1,2-difluoro-3-(4-fluoro-3-phenoxyphenyl)-1-propene, (Z)-;
1-[(p-fluoromethylphenyl)dimethylsilyl]-1,2-difluoro-3-(4-fluoro-3-phenoxyphenyl)-1-propene, (Z)-;
1-[(p-fluoromethylphenyl)dimethylsilyl]-1,2-difluoro-3-(p-chlorophenoxyphenyl)-1-propene, (Z)-; and
1-[(p-fluoromethylphenyl)dimethylsilyl]-1,2-difluoro-3-(p-flurophenoxyphenyl)-1-propene, (Z)-.

The product formula I compounds may be isolated by diluting the reaction mixture with water and extracting the product with a suitable extraction solvent. In the isolation procedure, conventional extraction solvents such as diethyl ether, ethyl acetate, toluene, methylene chloride, and the like, and mixtures thereof may be utilized.

Reducing agents suitable for use in the process of this invention include, but are not limited to, hydride reducing agents such as sodium bis(2-methoxyethoxy)-aluminum hydride, lithium aluminum hydride, and the like.

Lithium bases suitable for use in the process of this invention include, but are not limited to, alkyllithiums such as n-butyllithium, sec-butyllithium, tert-butyllithium, methyllithium, and the like; lithium dialkylamides such as lithium diisopropylamide, and the like; and lithium cyclicamides such as lithium tetramethylpiperidine, and the like.

First solvents suitable for use in the present invention include, but are not limited to, ethers such as tetrahydrofuran, diethyl ether, 1,4-dioxane, 1,2-dimethoxyethane, and the like; aromatic hydrocarbons such as toluene, benzene, xylenes, mesitylene, chlorobenzene, fluorobenzene, and the like; and mixtures thereof. Preferred first solvents include ethers.

Second solvents useful in the process of this invention include, but are not limited to, ethers such as diethyl ether, tetrahydrofuran, 1,2-dimethoxyethane, and the like, and mixtures thereof; and ether/hydrocarbon mixtures containing ethers such as diethyl ether, tetrahydrofuran, 1,2-dimethoxyethane, and the like, and mixtures thereof, and hydrocarbons such as hexane, pentane, heptane, and the like, and mixtures thereof.

Preferred formula I difluorovinylsilane compounds which may be prepared by the process of this invention are those wherein Ar is phenyl, optionally substituted with any combination of from one to three halogen, $C_1$–$C_4$alkyl, $C_1$–$C_4$halo-alkyl, $C_1$–$C_4$alkoxy or $C_1$–$C_4$haloalkoxy groups;

R and $R_1$ are each independently $C_1$–$C_4$alkyl; and $Ar_1$ is 3-phenoxyphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenyl, optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or biphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

The process of the present invention is also preferably used for the preparation of difluorovinyl-silane insecticide and acaricidal agents of formula I wherein Ar is phenyl, optionally substituted with any combination of from one to three halogen, $C_1$–$C_4$alkyl, $C_1$–$C_4$halo-alkyl, $C_1$–$C_4$alkoxy or $C_1$–$C_4$haloalkoxy groups;

R and $R_1$ are methyl; and $Ar_1$ is 3-phenoxyphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups. The 3-aryl-1,1,2-trilfluoro-1-propene compounds of formula II may be prepared by reacting a vinylorganometallic compound having the structural formula VII $$F_2C=CFM \quad\quad (VII)$$

wherein M is Cu, Li, ZnX or CdX, and X is Cl, Br or I with an α-(halomethyl)aryl compound having the structural formula VIII $$YCH_2Ar_1 \quad\quad (VIII)$$

wherein Y is Cl, Br or I, and $Ar_1$ is as described above for formula I.

In a preferred embodiment of this invention, the formula II compound is prepared by reacting (trifluoro-vinyl)copper with an α-(halomethyl)aryl compound of formula VIII in a presence of a polymerization inhibitor and substantially in the absence of light.

Polymerization inhibitors suitable for use include, but are not limited to, aromatic amines such as diphenylamines, and the like; substituted alkenes such as (+)-limonene, and the like; phenols such as 2,6-di-tert-butyl-4-methylphenol, and the like; and mixtures thereof.

In another preferred embodiment of the present invention, the formula II compound is prepared by reacting a halo (trifluorovinyl)zinc compound with an α-(halomethyl)aryl compound of formula VIII in the presence of a palladium catalyst. Palladium catalysts suitable for use in this invention include, but are not limited to, tetrakis (triphenylphosphine)palladium(0), bis (dibenzylideneacetone)palladium(0), bis(acetonitrile)-palladium(II) chloride, bis(triphenylphosphine)-palladium (II) chloride, [1,4-bis(diphenylphosphine)-butane]palladium (II) dichloride, [1,1'-bis(diphenyl-phosphino)ferrocene] palladium(II) diacetate, palladium(II) acetate, palladium(II) chloride, palladium on activated carbon, and the like, and mixtures thereof.

Preferably, the vinylorganometallic compound is reacted with the α-(halomethyl)aryl compound in the presence of an aprotic solvent, preferably at a temperature ranging about −30° C. to 100° C., more preferably from about 0° C. to 60° C. Aprotic solvents suitable for use include, but are not limited to, tetrahydrofuran, N,N-dimethylformamide, acetonitrile, diglyme, triglyme, tetraglyme, N,N-dimethylacetamide, and the like, and mixtures thereof.

Formula VII vinylorganometallic compounds are known in the art (see, e.g., *J. Org. Chem.*, 53, pp. 2714–2720 (1988); *J. Am. Chem. Soc.*, 108, pp. 4229–4230 (1986); and Tetrahedron, 50(10), pp. 2293–3063 (1994)).

In order to facilitate a further understanding of the invention, the following examples are presented primarily for the purpose of illustrating more specific details thereof. The scope of the invention should not be deemed limited by the examples, but encompasses all the subject matter defined in the claims.

EXAMPLE 1

Preparation of 1.2-Difluoro-3-(4-fluoro-3-phenoxyphenyl)-1-propene, (E)-

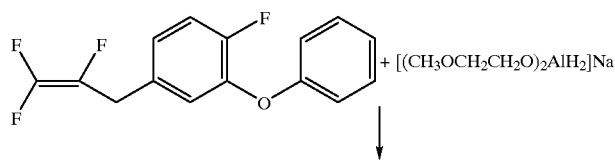

-continued

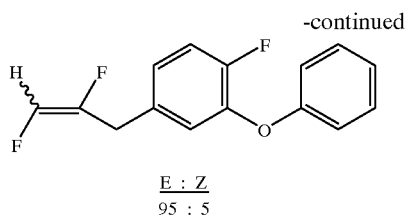

E : Z
95 : 5

A solution of 1,1,2-trifluoro-3-(4-fluoro-3-phenoxyphenyl)-1-propene (17.7 g, 0.0627 mol) in tetrahydrofuran (90 ml) is added dropwise over a period of 15 minutes to an ice cooled mixture of tetrahydrofuran (90 ml) containing 18.8 ml (0.0627 mol) of a 65 wt. % solution of sodium bis(2-methoxyethoxy)aluminum hydride in toluene. After stirring at room temperature for 20 hours, the resultant mixture is cooled, treated sequentially with ethyl acetate, water and dilute hydrochloric acid, and diluted with diethyl ether. The organic layer is separated, washed with brine, dried over anhydrous magnesium sulfate, and concentrated in vacuo to give the title product as a yellow liquid (16.08 g, 97% yield). $^1$H NMR analysis shows this material to be a 95:5 mixture of E:Z isomers.

EXAMPLE 2

Preparation of 1-[(p-Chlorophenyl)dimethylsilyl]-1,2-difluoro-3-(4-fluoro-3-phenoxyphenyl)-1-propene. (Z)-

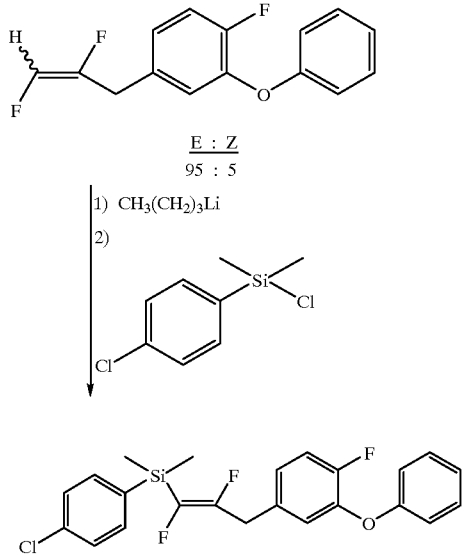

A −65° C. solution of 1,2-difluoro-3-(4-fluoro-3-phenoxyphenyl)-1-propene, (95:5 E/Z) (12.0 g, 0.0454 mol) in tetrahydrofuran (120 ml) is treated dropwise with a 2.5M solution of n-butyllithium in hexane (21.8 ml, 0.0545 mol) while maintaining the reaction mixture temperature below −55° C., stirred at −65° C. for 30 minutes, treated dropwise with a solution of p-chlorophenyl-dimethylsilyl chloride in tetrahydrofuran (15 ml) over a period of 3 minutes, stirred at −65° C. for 2.5 hours, and diluted with dilute hydrochloric acid and ether. After warming to room temperature, the organic layer is separated, washed with brine, dried over anhydrous magnesium sulfate, and concentrated in vacuo to obtain a residue. The residue is subjected to Kugelrohr distillation to remove volatiles and purified by flash chromatography on silica gel (elution with hexanes) to give the title product as a pale, yellow syrup (10.08 g, 51% yield).

EXAMPLE 3

Preparation of 1,1,2-Trifluoro-3-(4-fluoro-3-phenoxyphenyl1)-1-propene via (Trifluorovinyl) copper

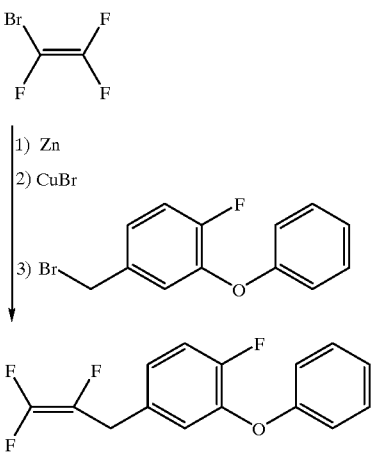

To a mixture of zinc dust (13.1 g, 0.2 mol) in N,N-dimethylformamide (150 ml) under a dry ice condenser is added bromotrifluoroethylene (40.0 g, 0.25 mol) via a gas inlet tube. The resultant reaction mixture is heated at 50° C. for 1.5 hours, vacuum distilled to remove excess bromotrifluoroethylene, cooled, and filtered to remove solids. The filtrate is treated with cuprous bromide (28.7 g, 0.2 mol), stirred in the dark for 30 minutes, treated sequentially with (+)-limonene (10 drops), phenothiazine (0.1 g) and α-bromo-4-fluoro-3-phenoxytoluene (28.1 g, 0.1 mol), heated at 50° C. in the dark for 17 hours, cooled, and poured into a mixture of saturated aqueous ammonium chloride (500 ml) and concentrated ammonium hydroxide (100 ml). The resultant aqueous mixture is extracted with 1:1 ether/petroleum ether, and the combined organic extracts are washed with brine, dried over anhydrous magnesium sulfate, and concentrated in vacuo to obtain a dark liquid. Flash chromatography of the liquid on silica gel (elution with hexanes) gives the title product as a clear liquid (15.16 g, 54% yield).

EXAMPLE 4

Preparation of 1,1,2-Trifluoro-3-(4-fluoro-3-phenoxyphenyl)-1-propene via Bromo (trifluorovinyl)zinc

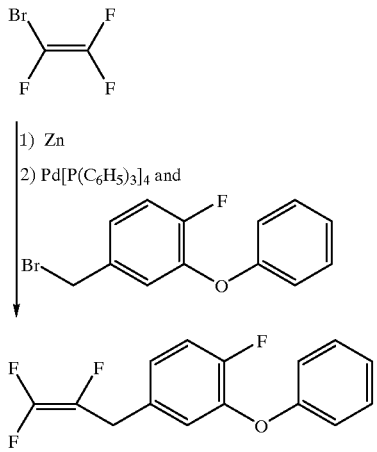

To a mixture of zinc dust (3.27 g, 0.05 mol) in N,N-dimethylformamide (40 ml) under a dry ice condenser is added bromotrifluoroethylene (9.61 g, 0.06 mol) via a gas inlet tube. The resultant reaction mixture is heated at 50° C. for 1.5 hours, vacuum distilled to remove excess bromotrifluoroethylene, cooled, and filtered to remove solids. The resultant filtrate is treated sequentially with tetrakis (triphenylphosphine)palladium(o) (0.58 g, 0.0005 mol) and α-bromo-4-fluoro-3-phenoxytoluene (5.62 g, 0.02 mol), heated at 80° C. for 2 hours, cooled to room temperature, and diluted with 10% aqueous HCl (150 ml). The resultant aqueous mixture is extracted with 1:1 ether/petroleum ether, and the combined organic extracts are washed sequentially with water and brine, dried over anhydrous magnesium sulfate, and concentrated in vacuo to obtain a residue. Flash chromatography of the residue on silica gel (elution with hexanes) gives the title product as a clear liquid (0.80 g, 14% yield).

We claim:

1. A process for the preparation of a difluoro-vinylsilane compound of the formula

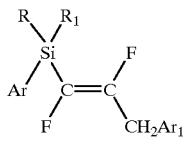

wherein

Ar is phenyl, optionally substituted with any combination of from one to three halogen, $C_1$–$C_4$alkyl, $C_1$–$C_4$haloalkyl, $C_1$–$C_4$alkoxy, $C_1$–$C_4$haloalkoxy, C(O) $R_2$ or $S(O)_nR_3$ groups, 1- or 2-naphthyl, optionally substituted with any combination of from one to three halogen, $C_1$–$C_4$alkyl, $C_1$–$C_4$haloalkyl, $C_1$–$C_4$alkoxy, $C_1$–$C_4$haloalkoxy, $C(O)R_2$ or $S(O)_nR_3$ groups, or a 5- or 6-membered heteroaromatic ring, optionally substituted with any combination of from one to three halogen, $C_1$–$C_4$alkyl, $C_1$–$C_4$haloalkyl, $C_1$–$C_4$alkoxy, $C_1$–$C_4$haloalkoxy, $C(O)R_2$ or $S(O)_nR_3$ groups;

R and $R_1$ are each independently $C_1$–$C_4$alkyl or $C_3$–$C_5$cycloalkyl;

$Ar_1$ is phenoxyphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, phenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, biphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, phenoxypyridyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, benzylpyridyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, benzylphenyl, optionally substituted with any combination of from one to five halogen, $C_1$–$C_4$alkyl, $C_1$–$C_4$haloalkyl, $C_1$–$C_4$alkoxy, $C_1$–$C_4$haloalkoxy or $C(O)R_4$ groups, 1- or 2-naphthyl, optionally substituted with any combination of from one to three halogen, $C_1$–$C_4$alkyl, $C_1$–$C_4$haloalkyl, $C_1$–$C_4$alkoxy, $C_1$–$C_4$haloalkoxy or $C(O)R_4$ groups, or a 5- or 6-membered heteroaromatic ring, optionally substituted with any combination of from one to three halogen, $C_1$–$C_4$alkyl, $C_1$–$C_4$haloalkyl, $C_1$–$C_4$alkoxy, $C_1$–$C_4$haloalkoxy or $C(O)R_4$ groups;

n is an integer of 0, 1 or 2;

$R_2$ and $R_4$ are each independently $C_1$–$C_4$alkyl, benzyl or phenyl; and $R_3$ is $C_1$–$C_4$alkyl or $C_1$–$C_4$haloalkyl; and the fluorine atoms attached to the double bond are trans with respect to each other, which process comprises:

(a) reacting a 3-aryl-1,1,2-trifluoro-1-propene compound of the formula

$F_2C\!=\!CFCH_2Ar_1$ wherein $Ar_1$ is as described above with a reducing agent to form a 3-aryl-1,2-difluoro-1-propene compound of the formula

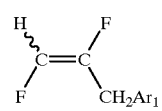

wherein the fluorine atoms attached to the double bond are predominately trans with respect to each other;

(b) reacting the 3-aryl-1,2-difluoro-1-propene compound with a lithium base to form a 3-aryl-1,2-difluoro-1-propenyllithium compound of the formula

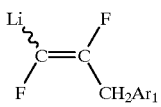

wherein the fluorine atoms attached to the double bond are predominately trans with respect to each other; and (c) reacting the 3-aryl-1,2-difluoro-1-propenyl-lithium compound with an arylchlorosilane compound of the formula

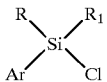

wherein Ar, R and $R_1$ are as described above.

2. The process according to claim 1 wherein the reducing agent is a hydride reducing agent, and the lithium base is selected from the group consisting of an alkyllithium, a lithium dialkylamide and a lithium cyclicamide.

3. The process according to claim 2 wherein the hydride reducing agent is selected from the group consisting of sodium bis(2-methoxyethoxy)aluminum hydride and lithium aluminum hydride, and the lithium base is selected from the group consisting of n-butyllithium, sec-butyllithium, tert-butyllithium, methyllithium, lithium disssopropylamide and lithium tetramethyl-piperidine.

4. The process according to claim 1 wherein the 3-aryl-1,1,2-trifluoro-1-propene compound is reacted with the reducing agent in the presence of a first solvent selected from the group consisting of an ether and an aromatic hydrocarbon and mixtures thereof, and the 3-aryl-1,2-difluoro-1-propene compound is reacted with the lithium base in the presence of a second solvent selected from the group consisting of an ether and an ether/hydrocarbon mixture.

5. The process according to claim 4 wherein the first solvent is selected from the group consisting of tetrahydrofuran, diethyl ether, 1,4-dioxane and 1,2-dimethoxyethane and mixtures thereof, and the second solvent is selected from the group consisting of diethyl ether, tetrahydrofuran, 1,2-dimethoxyethane and mixtures thereof and mixtures with hexane, pentane and/or heptane.

6. The process according to claim 1 wherein the 3-aryl-1,2-difluoro-1-propenyllithium compound is reacted in situ with the arylchlorosilane compound.

7. The process according to claim 1 wherein step (a) is conducted at a temperature of about −50° C. to 50° C., step (b) is conducted at a temperature of about −100° C. to 0° C., and step (c) is conducted at a temperature of about −100° C. to 50° C.

8. The process according to claim 7 wherein step (a) is conducted at a temperature of about −10° C. to 25° C., step (b) is conducted at a temperature of about −70° C. to −50° C., and step (c) is conducted at a temperature of about −70° C. to 30° C.

9. The process according to claim 1 wherein

Ar is phenyl, optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently $C_1$–$C_4$alkyl; and $Ar_1$ is 3-phenoxyphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenyl, optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or biphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

10. The process according to claim 9 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are methyl; and $Ar_1$ is 3-phenoxyphenyl, optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

11. The process according to claim 1 for the preparation of a compound selected from the group consisting of 1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl)dimethylsilyl]-1,2-difluoro-1-propene, (Z)-;

1,2-difluoro-3-(4-fluoro-3-phenoxyphenyl)-1-[(p-fluorophenyl)dimethylsilyl]-1-propene, (Z)-;

1,2-difluoros-1-(phenyldimethylsilyl)-3-(4-fluoro-3-phenoxyphenyl)-1-propene, (Z)-;

1-[(p-trifluoromethylphenyl)dimethylsilyl]-1,2-difluoro-3-(4-fluoro-3-phenoxyphenyl)-1-propene, (Z)-;

1-[(p-trifluoromethoxphenyl)dimethylsilyl]-1,2-difluoro-3-(4-fluoro-3-phenoxyphenyl)-1-propene, (Z)-;

1-[(p-fluoromethylphenyl)dimethylsilyl]-1,2-difluoro-3-(4-fluoro-3-phenoxyphenyl)-1-propene, (Z)-;

1-[(p-fluoromethylphenyl)dimethylsilyl]-1,2-difluoro-3-(p-chlorophenoxyphenyl)-1-propene, (Z)-; and 1-[(p-fluoromethylphenyl)dimethylsilyl]-1,2-difluoro-3-(p-flurophenoxyphenyl)-1-propene, (Z)-.

* * * * *